United States Patent
Ci

(10) Patent No.: US 10,548,934 B2
(45) Date of Patent: Feb. 4, 2020

(54) CHINESE HERBAL ORAL PASTE FOR KEEPING BALANCED CONSTITUTION AND PROCESSING METHOD THEREOF

(71) Applicant: Zhonghua Ci, Beijing (CN)

(72) Inventor: Zhonghua Ci, Beijing (CN)

(*) Notice: Subject to any disclaimer, the term of this patent is extended or adjusted under 35 U.S.C. 154(b) by 0 days.

(21) Appl. No.: 15/967,129

(22) Filed: Apr. 30, 2018

(65) Prior Publication Data

US 2019/0192599 A1    Jun. 27, 2019

(30) Foreign Application Priority Data

Dec. 26, 2017    (CN) .......................... 2017 1 1429051

(51) Int. Cl.
| | | |
|---|---|---|
| *A61K 36/00* | (2006.01) | |
| *A61K 36/344* | (2006.01) | |
| *A61K 36/076* | (2006.01) | |
| *A61K 36/236* | (2006.01) | |
| *A61K 36/638* | (2006.01) | |
| *A61K 36/8945* | (2006.01) | |
| *A61K 36/481* | (2006.01) | |
| *A61K 36/734* | (2006.01) | |
| *A61K 36/8994* | (2006.01) | |
| *A61K 36/752* | (2006.01) | |
| *A61K 35/586* | (2015.01) | |
| *A61K 47/26* | (2006.01) | |
| *A61K 45/06* | (2006.01) | |
| *A61P 25/24* | (2006.01) | |
| *A61K 9/00* | (2006.01) | |
| *A61K 36/284* | (2006.01) | |

(52) U.S. Cl.
CPC .......... *A61K 36/344* (2013.01); *A61K 9/0053* (2013.01); *A61K 35/586* (2013.01); *A61K 36/076* (2013.01); *A61K 36/236* (2013.01); *A61K 36/284* (2013.01); *A61K 36/481* (2013.01); *A61K 36/638* (2013.01); *A61K 36/734* (2013.01); *A61K 36/752* (2013.01); *A61K 36/8945* (2013.01); *A61K 36/8994* (2013.01); *A61K 45/06* (2013.01); *A61K 47/26* (2013.01); *A61P 25/24* (2018.01); *A61K 2236/13* (2013.01); *A61K 2236/51* (2013.01)

(58) Field of Classification Search
None
See application file for complete search history.

*Primary Examiner* — Qiuwen Mi
(74) *Attorney, Agent, or Firm* — Novick, Kim & Lee, PLLC; Allen Xue

(57) ABSTRACT

The present application discloses a Chinese herbal oral paste for keeping balanced constitution. The Chinese herbal oral paste includes the following raw material components: tangshen, largehead atractylodes rhizome, fuling, prepared liquorice root, glossy privet fruit, *polygonatum odoratum*, dwarf lilyturf tuber, flatstem milkvetch seed, Chinese yam, unprocessed hawthorn fruit, prepared fleeceflower root, milkvetch root, dried tangerine peel, angelica, *dendrobium*, Chinese arborvitae kernel, root and vine of manyprickle acanthopanax, radix asparagi, danshen root, figwort root, gorgon euryale seeds, villous amomum fruit, coix seed, mulberry fruit, fruit of Chinese magnoliavine, lilium brownii, prepared milkwort root, barbary wolfberry fruit, donkey-hide gelatin, tortoise-plastron gelatin, and xylitol. The Chinese herbal oral paste of the present disclosure has a higher drug concentration and good taste, is particularly suitable for health preserving in winter and conditioning the balanced constitution, will not create negative effects or harm to the human body at all, and is capable of achieving certain efficacy of strengthening physical health.

20 Claims, 1 Drawing Sheet

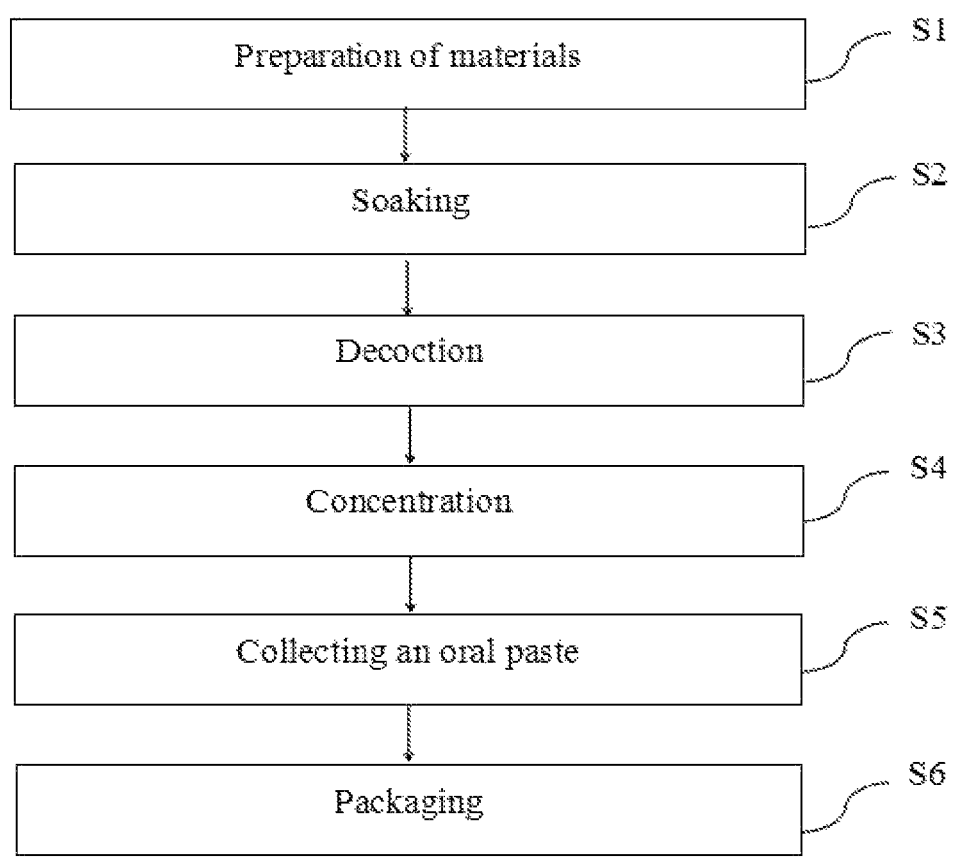

CHINESE HERBAL ORAL PASTE FOR KEEPING BALANCED CONSTITUTION AND PROCESSING METHOD THEREOF

TECHNICAL FIELD

The present disclosure relates to the field of health foods, and particularly to a Chinese herbal oral paste for keeping balanced constitution and a processing method thereof.

BACKGROUND

In *Classification and Determination of Constitution in Traditional Chinese Medicine*, the China Association of Chinese Medicine classifies body constitutions of the human body into nine types, i.e., balanced constitution (yin-yang harmony constitution), yang deficiency constitution, yin deficiency constitution, qi deficiency constitution, phlegm-dampness constitution, damp-heat constitution, qi depression constitution, blood stasis constitution, and allergic constitution, most of which are sub-healthy states.

The balanced constitution is such a constitution status mainly featured by moderate posture, rosy facial complexion, vigorousness, healthy and robust functions and states of internal organs (zang and fu), also called as "mild constitution". The population with balanced constitution occupies about 32.75%. More men than women have the balanced constitution, moreover, the number of people having the balanced constitution get decreased with the increasing age.

People having the balanced constitution have a well-proportioned, healthy and strong body configuration, easy-going and optimistic personality, moisturizing and lustrous facial complexion and skin color, dense and glossy hairs, bright eyes, bright and lubricating nose color, acute sense of smell, normal sense of taste, ruddy lip color, vigorousness, indefatigability, cold-resistance and heat-resistance, sound sleep, good appetite, regular defecation, reddish tongue color, thin and white tongue fur, gentle pulse, less illness usually, and strong adaptability to natural environments and social environments.

It is mentioned in the Inner Canon of the Yellow Emperor that "the superior physician prevents illness, the mediocre physician attends to impending illness, and the inferior physician treats actual illness", wherein the phrase "prevent illness" means taking corresponding measures to prevent the occurrence and development of diseases. The body constitution determines the health of people and determines the susceptibility to diseases. It is believed in the traditional Chinese medicine that since the human beings live in the natural world, physiological functions of the human body usually change with seasons, that is, "correspondence between man and nature". Winter is the season when the human body "stores energies", and appropriate nourishment can enhance the constitution, ward off diseases and strengthen the body, and prolong life, that is, conditioning in winter or nourishing in winter commonly mentioned in the traditional Chinese medicine. In order to keep or have the balanced constitution, to choose a solid oral paste with a higher drug concentration and good taste, and being convenient to carry is more adapted to requirements of modern people.

SUMMARY

A main object of the present disclosure is to provide a Chinese herbal nourishing product suitable for conditioning in winter so as to keep the balanced constitution.

In order to achieve the above object, according to one aspect of the present disclosure, there is provided a Chinese herbal oral paste for keeping balanced constitution.

The Chinese herbal oral paste for keeping balanced constitution according to the present disclosure includes the following raw material components in parts by weight: 6-18 parts of tangshen, 5-15 parts of largehead atractylodes rhizome, 8-22 parts of fuling, 2-10 parts of prepared liquorice root, 7-23 parts of glossy privet fruit, 5-15 parts of polygonatum odoratum, 5-15 parts of dwarf lilyturf tuber, 5-15 parts of flatstem milkvetch seed, 6-18 parts of Chinese yam, 6-18 parts of unprocessed hawthorn fruit, 7-23 parts of prepared fleeceflower root, 5-15 parts of milkvetch root, 5-15 parts of dried tangerine peel, 5-15 parts of angelica, 8-22 parts of dendrobium, 6-14 parts of Chinese arborvitae kernel, 7-17 parts of root and vine of manyprickle acanthopanax, 5-16 parts of radix asparagi, 5-15 parts of danshen root, 6-14 parts of figwort root, 5-14 parts of gorgon euryale seeds, 1-5 parts of villous amomum fruit, 6-18 parts of coix seed, 7-23 parts of mulberry fruit, 3-14 parts of fruit of Chinese magnoliavine, 4-16 parts of lilium brownii, 3-9 parts of prepared milkwort root, 7-23 parts of barbary wolfberry fruit, 10-30 parts of donkey-hide gelatin, 10-30 parts of tortoise-plastron gelatin, and 10-30 parts of xylitol.

Furthermore, the Chinese herbal oral paste for keeping balanced constitution according to the present disclosure includes the following raw material components in parts by weight: 9-15 parts of tangshen, 8-12 parts of largehead atractylodes rhizome, 11-19 parts of fuling, 4-8 parts of prepared liquorice root, 11-19 parts of glossy privet fruit, 8-12 parts of polygonatum odoratum, 8-12 parts of dwarf lilyturf tuber, 8-12 parts of flatstem milkvetch seed, 9-15 parts of Chinese yam, 9-15 parts of unprocessed hawthorn fruit, 11-19 parts of prepared fleeceflower root, 8-12 parts of milkvetch root, 8-12 parts of dried tangerine peel, 8-12 parts of angelica, 12-18 parts of dendrobium, 8-12 parts of Chinese arborvitae kernel, 9-15 parts of root and vine of manyprickle acanthopanax, 8-12 parts of radix asparagi, 8-12 parts of danshen root, 8-12 parts of figwort root, 8-12 parts of gorgon euryale seeds, 2-4 parts of villous amomum fruit, 9-15 parts of coix seed, 11-19 parts of mulberry fruit, 5-11 parts of fruit of Chinese magnoliavine, 8-12 parts of lilium brownii, 5-7 parts of prepared milkwort root, 12-18 parts of barbary wolfberry fruit, 15-25 parts of donkey-hide gelatin, 15-25 parts of tortoise-plastron gelatin, and 15-25 parts of xylitol.

Furthermore, the Chinese herbal oral paste for keeping balanced constitution according to the present disclosure includes the following raw material components in parts by weight: 12 parts of tangshen, 10 parts of largehead atractylodes rhizome, 15 parts of fuling, 6 parts of prepared liquorice root, 15 parts of glossy privet fruit, 10 parts of polygonatum odoratum, 10 parts of dwarf lilyturf tuber, 10 parts of flatstem milkvetch seed, 12 parts of Chinese yam, 12 parts of unprocessed hawthorn fruit, 15 parts of prepared fleeceflower root, 10 parts of milkvetch root, 10 parts of dried tangerine peel, 10 parts of angelica, 15 parts of dendrobium, 10 parts of Chinese arborvitae kernel, 12 parts of root and vine of manyprickle acanthopanax, 10 parts of radix asparagi, 10 parts of danshen root, 10 parts of figwort root, 10 parts of gorgon euryale seeds, 3 parts of villous amomum fruit, 12 parts of coix seed, 15 parts of mulberry fruit, 8 parts of fruit of Chinese magnoliavine, 10 parts of lilium brownii, 6 parts of prepared milkwort root, 15 parts of barbary wolfberry fruit, 20 parts of donkey-hide gelatin, 20 parts of tortoise-plastron gelatin, and 20 parts of xylitol.

In order to achieve the above object, according to the other aspect of the present disclosure, there is provided a processing method for a Chinese herbal oral paste for keeping balanced constitution.

The processing method for a Chinese herbal oral paste for keeping balanced constitution according to the present disclosure includes the following steps in sequence: preparation of materials, soaking, decoction, concentration, and collecting an oral paste.

Furthermore, the step of preparation of materials is: measuring raw materials of formula amounts according to composition of the Chinese herbal oral paste, and cleaning raw materials, except tortoise-plastron gelatin, donkey-hide gelatin, and xylitol, for subsequent use.

Furthermore, the soaking step is: soaking the cleaned raw materials with 8-10 folds of water for 8-15 h, with the water over the raw materials by 10-20 cm.

Furthermore, the decoction step is: decocting the soaked drug materials over flame, firstly boiling the drug materials with high heat to sufficiently expand, then boiling the drug materials with low heat for 1-2 hours of decoction, then filtering the drug juice with gauze, then soaking filtered dregs of decoction with clear water and decocting the soaked dregs of decoction with low heat for 1 hour, repeated 2-4 times, combining the filtered drug juice, and squeezing and filtering the dregs to obtain a squeezed juice; combining decoction juice with the squeezed juice, followed by static settlement for 2 h, and filtering, to obtain a supernatant liquid for subsequent use.

Furthermore, the concentration step is: boiling and skimming the supernatant liquid resulted in the decoction step, followed by decoction concentration and stirring with gentle heat, until the drug liquid does not disperse when being dropped on paper, to obtain a vegetarian paste.

Furthermore, the step of collecting an oral paste is: pouring xylitol, and melted tortoise-plastron gelatin and donkey-hide gelatin into the vegetarian paste respectively, cooking them slowly with low heat, stirring them continuously with a shovel, until the juice coagulates into beads when dropped into clear water and does not disperse, and canning the resulted oral paste.

The melting step is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

The Chinese herbal oral paste of the present disclosure has a higher drug concentration and good taste, is particularly suitable for health preserving in winter and conditioning the balanced constitution, will not create negative effects or harm to the human body at all, and is capable of achieving certain efficacy of strengthening physical health.

BRIEF DESCRIPTION OF THE DRAWINGS

The accompanying drawing, which constitutes a part of the present application, is used to provide a further understanding of the present disclosure, so that other features, objects, and advantages of the present application become more obvious. The illustrative drawings for embodiments of the present disclosure and the description thereof are used to explain the present disclosure, rather than constitute an improper limitation on the present disclosure. In the drawing, FIG. 1 is a flow chart of a processing technology for a Chinese herbal oral paste of an embodiment of the present disclosure.

DETAILED DESCRIPTION OF THE EMBODIMENTS

In order to enable a person skilled in the art to better understand the solutions of the present application, the technical solutions of the embodiments of the present disclosure will be described clearly and completely below with reference to the accompanying drawing of the embodiments of the present application. Apparently, the embodiments described are merely for some of the embodiments of the present application, rather than all of the embodiments. All the other embodiments that are obtained by a person skilled in the art without inventive effort on the basis of the embodiments of the present application shall be covered by the protection scope of the present application.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the embodiments of the present application and the features of the embodiments can be combined with each other if there is no conflict. The present application will be described in detail below in combination with the embodiments.

The present disclosure provides a Chinese herbal oral paste for keeping balanced constitution, including the following raw material components: tangshen, largehead atractylodes rhizome, fuling, prepared liquorice root, glossy privet fruit, polygonatum odoratum, dwarf lilyturf tuber, flatstem milkvetch seed, Chinese yam, unprocessed hawthorn fruit, prepared fleeceflower root, milkvetch root, dried tangerine peel, angelica, dendrobium, Chinese arborvitae kernel, root and vine of manyprickle acanthopanax, radix asparagi, danshen root, figwort root, gorgon euryale seeds, villous amomum fruit, coix seed, mulberry fruit, fruit of Chinese magnoliavine, lilium brownii, prepared milkwort root, barbary wolfberry fruit, donkey-hide gelatin, tortoise-plastron gelatin, and xylitol.

Tangshen is sweet in flavor and neutral in nature, acts on spleen and lung, nourishes the middle energizer and supplements qi, harmonizes stomach and promotes the secretion of body fluid, eliminates phlegm and relieves cough, and is used for reduced spleen-deficiency appetite and loose stool, numbness of limbs, palpitation, shortness of breath, mouth dryness, spontaneous perspiration, rectocele, and prolapse of the uterus.

Largehead atractylodes rhizome is bitter and sweet in flavor and warm in nature, acts on spleen and stomach, tonifies spleen and supplements qi, dries dampness and alleviates water retention, constrains sweating, prevents miscarriage, and is used for reduced spleen-deficiency appetite, abdominal distension diarrhea, phlegm and fluid retention and palpitation, edema, spontaneous perspiration, and fetal upset.

Fuling is sweet and light in flavor and neutral in nature, acts on heart, lung, spleen, and kidney, alleviates water retention and clears dampness, tonifies spleen, calms the mind, and is used for edema and scanty urine, phlegm and fluid retention and dizziness and palpitation, reduced spleen-deficiency appetite, loose stool and diarrhea, uneasiness, and palpitation to insomnia.

Prepared liquorice root is sweet in flavor and neutral in nature, acts on heart, lung, spleen, and stomach, nourishes spleen and harmonizes stomach, supplements qi and restores pulse, and is used for spleen and stomach weakness, tiredness, palpitation, and irregular pulse.

Glossy privet fruit is sweet and bitter in flavor and cool in nature, acts on liver and kidney, nourishes liver and kidney, improves eyesight, clears away asthenic fever, and is used for dizziness, premature graying of hair, blurred vision, and fever due to yin deficiency.

Polygonatum odoratum is sweet in flavor and neutral in nature, acts on lung and stomach, nourishes yin, moistens lung, promotes the secretion of body fluid and quenches thirst, and is used for lung and stomach yin injury, dryness-heat cough, throat dryness and thirst, and internal-heat consumptive thirst.

Dwarf lilyturf tuber is sweet and slightly bitter in flavor and slightly cold in nature, acts on stomach, lung, and heart, nourishes yin and moistens lung, benefits stomach and promotes the secretion of body fluid, clears away the heart fire and relieves restlessness, and is used for lung-dryness dry cough, yin-deficiency consumptive cough, laryngeal paralysis and pharyngalgia, body fluid impairment thirst, internal-heat consumptive thirst, dysphoria insomnia, constipation due to intestinal dryness and so on.

Flatstem milkvetch seed is sweet in flavor and warm in nature, acts on liver and kidney, tonifyes kidney to secure essence, clears liver to improve eyesight, and is used for soreness and weakness of waist and knees, gonobolia and premature ejaculation, enuresis, frequent urination, leucorrhea disease, neurasthenia and hypopsia, diabetes and so on.

Chinese yam is sweet in flavor, neutral in nature, and non-toxic, acts on spleen, lung, and kidney, strengthens spleen and stomach, nourishes lung qi, tonifies kidney essence, nourishes physical health, renders good hearing and eyesight and delays senility upon long administration, and is used for reduced spleen-deficiency appetite, loose stool diarrhea, lung-deficiency asthma, gonobolia and frequent urination, and yin-deficiency consumptive thirst.

Unprocessed hawthorn fruit is sour and sweet in flavor, and slightly warm in nature, acts on spleen, stomach, and liver, promotes digestion and tonifies stomach, promotes the circulation of qi to dissipate stasis, resolves turbidity and lowers lipid, and is used for meat-type food accumulation, abdominal fullness and distention, dysentery abdominal pain, blood stasis amenorrhea, puerperal blood stasis, prickling in heart and abdomen, chest stuffiness and pains, colic pain, and hyperlipemia.

Prepared fleeceflower root is bitter, astringent and sweet in flavor and slightly warm in nature, acts on liver, heart, and kidney, nourishes liver and kidney, tonifies essence and blood, blackens hair and beard, strengthens muscles and bones, resolves turbidity and lowers lipid, and is used for blood-deficiency etiology, vertigo and tinnitus, premature graying of hair, soreness and weakness of waist and knees, numbness of limb, metrorrhagia and leucorrhoea, and hyperlipemia.

Milkvetch root is sweet in flavor and slightly warm in nature, acts on lung, spleen, liver, and kidney, tonifies defensive-qi and secures the exterior, replenishes qi and invigorates yang, draws toxin and promotes tissue generation, alleviates water retention and relieves swelling, and is used for qi-deficiency lassitude, reduced appetite and loose stool, sinking of middle qi, rectocele due to chronic diarrhea, spontaneous perspiration and night sweating, blood-deficiency etiology, dorsal furuncle borderless swelling, qi-deficiency edema, and internal-heat consumptive thirst.

Dried tangerine peel is bitter and acrid in flavor and warm in nature, acts on lung and spleen, regulates qi and tonifies spleen, dries dampness and resolves phlegm, and is used for abdominal fullness and distention, reduced appetite and vomiting, and cough with excessive phlegm.

Angelica is sweet and acrid in flavor and warm in nature, acts on liver, heart, and spleen, replenishes blood and invigorates the circulation of blood, regulates menstruation and relieves pain, relaxes bowel, and is used for blood-deficiency etiology, vertigo and palpitation, irregular menstruation, amenorrhea and dysmenorrhea, deficiency-cold stomachache, rheumatic arthralgia, traumatic injury, ulcer and skin and external diseases, and constipation due to intestinal dryness.

Dendrobium is sweet flavor and slightly cold in nature, acts on stomach and kidney, benefits stomach and promotes the generation of body fluid, nourishes yin and clears away heat, and is used for febrile disease and body fluid impairment, mouth dryness and polydipsia, stomach yin insufficiency, reduced appetite and vomiturition, persistent deficiency-heat after illness, yin-deficiency fire excess, steaming bone consumptive fever, blurred vision, and motor impairment of muscles and bones.

Chinese arborvitae kernel is sweet in flavor and neutral in nature, acts on heart, kidney, and large intestine, nourishes heart to tranquilize the spirit, relaxes bowel, resists sweating, and is used for yin blood insufficiency, dysphoria and insomnia, palpitation, constipation due to intestinal dryness, and yin-deficiency night sweating.

Root and vine of manyprickle acanthopanax are acrid and slightly bitter in flavor and warm in nature, acts on spleen, kidney, and heart, tonifies kidney and waist, supplements qi to calm mind, promotes blood circulation to remove meridian obstruction, and is used for kidney-deficiency body weakness, soreness and weakness of waist and knees, retardation in walking of infants, spleen-deficiency asthenia, qi-deficiency edema, poor appetite, insomnia and dreamful sleep, amnesia, chest obstruction and pain, wind-cold-dampness arthralgia, and traumatic gall.

Radix asparagi is sweet and bitter in flavor and cold in nature, acts on lung and kidney, nourishes yin and moistens dryness, clears lung and promotes the secretion of body fluid, and is used for lung-dryness dry cough, pertussis and sticky phlegm, soreness and ache of waist and knees, steaming bone hectic fever, internal heat consumptive thirst, febrile disease and body fluid impairment, throat dryness and thirst, and constipation due to intestinal dryness.

Danshen root is bitter in flavor and slightly cold in nature, acts on heart and liver, invigorates blood circulation to remove blood stasis, induces menstruation to stop pain, clears away the heart fire and relieves restlessness, cools blood to resolve carbuncle, and is used for chest stuffiness and pains, abdominal fullness and hypochondriac pain, mass in abdomen, heat arthralgia pain, dysphoria insomnia, irregular menstruation, dysmenorrhea and amenorrhea, and swelling pain of skin and external diseases.

Figwort root is bitter and salty in flavor and slightly cold in nature, acts on lung and kidney, nourishes yin to lessen fire, cools blood to remove toxic matters, and is used for febrile disease and body fluid impairment, polydipsia, eruption, constipation due to intestinal dryness, yin-deficiency steaming bone consumptive fever, difficult sleep, spontaneous perspiration and night sweating, hematemesis, bleeding from five sense organs or subcutaneous tissue, swollen sore throat, red eyes, carbuncle, and scrofula.

Gorgon euryale seeds are sweet and astringent in flavor and neutral in nature, acts on spleen and kidney, tonify kidney to secure essence, nourish spleen to cure diarrhea, dispel dampness to arrest leucorrhoea, and are used for gonobolia and spermatorrhea, enuresis and frequent urination, spleen-deficiency chronic diarrhea, gonorrhea, and leucorrhoea disease.

Villous amomum fruit is acrid in flavor and warm in nature, acts on spleen, stomach, and kidney, promotes the circulation of qi to regulate middle energizer, harmonizes stomach, refreshes spleen, and is used for abdominal pain and distension, anorexia and dyspepsia, dysphagia and vomiting, cold diarrhea and dysentery, and fetal movement.

Coix seed is sweet and light in flavor and cool in nature, acts on spleen, stomach, and lung, alleviates water retention and clears dampness, tonifies spleen to cure diarrhea, eliminates arthralgia syndromes, discharges pus, clears away toxic matters to remove stasis, and is used for edema, beriberi, difficult urination, spleen-deficiency diarrhea, dampness arthralgia muscular constriction, pulmonary abscess, intestinal carbuncle, excrescence, and cancerous protuberance.

Mulberry fruit is sweet in flavor and cold in nature, acts on heart, liver, and kidney, nourishes yin and replenishes blood, moistens intestines, promotes the secretion of body fluid, and is used for yin-deletion blood depletion, yin-deficiency consumptive thirst, body fluid deletion thirst, vertigo and tinnitus, and constipation due to intestinal dryness.

Fruit of Chinese magnoliavine is sour in flavor and warm in nature, acts on lung, kidney, and heart, astringes lung, nourishes kidney, promotes the secretion of body fluid, constrains sweating, arrests seminal emission, and is used for kidney-deficiency asthma, mouth dryness and thirst, spontaneous perspiration, night sweating, internal lesion caused by overexertion and emaciation, wet dream and spermatorrhea, and chronic diarrhea and dysentery.

Lilium brownii is sweet in flavor and cold in nature, acts on heart and lung, nourishes yin and moistens lung, clears away the heart fire and calms mind, and is used for yin-deficiency irritating dry cough, over-strained cough and hemoptysis, dysphoria and pavor, insomnia and dreamful sleep, and trance.

Milkwort root is bitter and acrid in flavor and warm in nature, acts on heart, kidney, and lung, calm the mind and develops intelligence, resolves depression, and is used for palpitation, amnesia, wet dream, insomnia, cough with excessive phlegm, and ulcer and skin and external diseases.

Barbary wolfberry fruit is sweet in flavor and neutral in nature, acts on the liver and kidney, nourishes the livers and kidneys, and replenishes vital essence to improve eyesight, and is used for syndromes of liver-kidney yin deficiency. Barbary wolfberry fruit is sweet and natural in flavor and moist, nourishes the liver and kidney, with the function of nourishing and building up the body, and can be applied to various syndromes of liver-kidney yin deficiency.

Donkey-hide gelatin is sweet in flavor and neutral in nature, acts on lung, liver, and kidney, replenishes blood and nourishes yin, moistens dryness, stops bleeding, and is used for blood-deficiency etiolation, vertigo and palpitation, dysphoria insomnia, and lung dryness cough.

Tortoise-plastron gelatin is sweet and salty in flavor and neutral in nature, nourishes yin, replenishes blood, stops bleeding, and is used for yin-deficiency blood depletion, consumptive heat and steaming bone, hematemesis, bleeding from five sense organs or subcutaneous tissue, dysphoria with smothery sensation and palpitation, kidney-deficiency backache, impotent feet and knees, metrorrhagia and metrostaxis, and leucorrhoea disease.

For people with the balanced constitution, the principle should be conditioning the balanced constitution and strengthening the body, so that the yin and yang of qi and blood in the body are maintained in an ordinary balanced and stable state. Drugs which are warm and nourish yin and yang of qi and blood should be used in the prescription. With the multiple types of drug materials of large dosages, the above oral paste prescription can enable efficacies of the various drug materials to generate a synergistic effect, with the functions of regulating yin and yang and balancing qi and blood, and can be used for keeping the balanced constitution, so that people are vigorous with strong resistibility and energetic, and the occurrence of diseases is avoided. With the conditioning for such constitution, it is more targeted and will not create side effects, without harm to the human body at all, and can achieve certain efficacy of strengthening the body.

As shown in FIG. 1, the processing method for the Chinese herbal oral paste for keeping balanced constitution of the present disclosure includes the following steps in sequence: preparation of materials, soaking, decoction, concentration, collecting an oral paste, and finally packaging. For specific operations of respective steps, reference can be made to various embodiments of the present disclosure.

Embodiment 1:

A Chinese herbal oral paste for keeping balanced constitution includes the following raw material components in parts by weight: 6 parts of tangshen, 5 parts of largehead atractylodes rhizome, 8 parts of fuling, 2 parts of prepared liquorice root, 7 parts of glossy privet fruit, 5 parts of polygonatum odoratum, 5 parts of dwarf lilyturf tuber, 5 parts of flatstem milkvetch seed, 6 parts of Chinese yam, 6 parts of unprocessed hawthorn fruit, 7 parts of prepared fleeceflower root, 5 parts of milkvetch root, 5 parts of dried tangerine peel, 5 parts of angelica, 8 parts of dendrobium, 6 parts of Chinese arborvitae kernel, 7 parts of root and vine of manyprickle acanthopanax, 5 parts of radix asparagi, 5 parts of danshen root, 6 parts of figwort root, 5 parts of gorgon euryale seeds, 1 parts of villous amomum fruit, 6 parts of coix seed, 7 parts of mulberry fruit, 3 parts of fruit of Chinese magnoliavine, 4 parts of lilium brownii, 3 parts of prepared milkwort root, 7 parts of barbary wolfberry fruit, 10 parts of donkey-hide gelatin, 10 parts of tortoise-plastron gelatin, and 10 parts of xylitol.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 8 folds of water for 8 h, with the water over the raw materials by 10 cm;

decoction: decocting the soaked drug materials over flame, firstly boiling the drug materials with high heat to sufficiently expand, then boiling the drug materials with low heat for 1 hour of decoction, then filtering the drug juice with gauze, then soaking filtered dregs of decoction with clear water and decocting the soaked dregs of decoction with low heat for 1 hour, repeated 4 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Embodiment 2:

A Chinese herbal oral paste for keeping balanced constitution includes the following raw material components in parts by weight: 18 parts of tangshen, 15 parts of largehead atractylodes rhizome, 22 parts of fuling, 10 parts of prepared liquorice root, 23 parts of glossy privet fruit, 15 parts of polygonatum odoratum, 15 parts of dwarf lilyturf tuber, 15 parts of flatstem milkvetch seed, 18 parts of Chinese yam, 18 parts of unprocessed hawthorn fruit, 23 parts of prepared fleeceflower root, 15 parts of milkvetch root, 15 parts of dried tangerine peel, 15 parts of angelica, 22 parts of dendrobium, 14 parts of Chinese arborvitae kernel, 17 parts of root and vine of manyprickle acanthopanax, 16 parts of radix asparagi, 15 parts of danshen root, 14 parts of figwort root, 14 parts of gorgon euryale seeds, 5 parts of villous amomum fruit, 18 parts of coix seed, 23 parts of mulberry fruit, 14 parts of fruit of Chinese magnoliavine, 16 parts of lilium brownii, 9 parts of prepared milkwort root, 23 parts of barbary wolfberry fruit, 30 parts of donkey-hide gelatin, 30 parts of tortoise-plastron gelatin, and 30 parts of xylitol.

The processing method therefor includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 10 folds of water for 15 h, with the water over the raw materials by 20 cm;

decoction: decocting the soaked drug materials over flame, firstly boiling the drug materials with high heat to sufficiently expand, then boiling the drug materials with low heat for 2 hours of decoction, then filtering the drug juice with gauze, then soaking filtered dregs of decoction with clear water and decocting the soaked dregs of decoction with low heat for 1 hour, repeated 2 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Embodiment 3:

A Chinese herbal oral paste for keeping balanced constitution includes the following raw material components in parts by weight: 9 parts of tangshen, 8 parts of largehead atractylodes rhizome, 11 parts of fuling, 4 parts of prepared liquorice root, 11 parts of glossy privet fruit, 8 parts of polygonatum odoratum, 8 parts of dwarf lilyturf tuber, 8 parts of flatstem milkvetch seed, 9 parts of Chinese yam, 9 parts of unprocessed hawthorn fruit, 11 parts of prepared fleeceflower root, 8 parts of milkvetch root, 8 parts of dried tangerine peel, 8 parts of angelica, 12 parts of dendrobium, 8 parts of Chinese arborvitae kernel, 9 parts of root and vine of manyprickle acanthopanax, 8 parts of radix asparagi, 8-12 parts of danshen root, 8 parts of figwort root, 8 parts of gorgon euryale seeds, 2 parts of villous amomum fruit, 9 parts of coix seed, 11 parts of mulberry fruit, 5 parts of fruit of Chinese magnoliavine, 8 parts of lilium brownii, 5 parts of prepared milkwort root, 12 parts of barbary wolfberry fruit, 15 parts of donkey-hide gelatin, 15 parts of tortoise-plastron gelatin, and 15 parts of xylitol.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 9 folds of water for 10 h, with the water over the raw materials by 15 cm;

decoction: decocting the soaked drug materials over flame, firstly boiling the drug materials with high heat to sufficiently expand, then boiling the drug materials with low heat for 1.5 hours of decoction, then filtering the drug juice with gauze, then soaking filtered dregs of decoction with clear water and decocting the soaked dregs of decoction with low heat for 1 hour, repeated 3 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Embodiment 4:

A Chinese herbal oral paste for keeping balanced constitution includes the following raw material components in parts by weight: 15 parts of tangshen, 12 parts of largehead atractylodes rhizome, 19 parts of fuling, 8 parts of prepared liquorice root, 19 parts of glossy privet fruit, 12 parts of polygonatum odoratum, 12 parts of dwarf lilyturf tuber, 12 parts of flatstem milkvetch seed, 15 parts of Chinese yam, 15 parts of unprocessed hawthorn fruit, 19 parts of prepared fleeceflower root, 12 parts of milkvetch root, 12 parts of dried tangerine peel, 12 parts of angelica, 18 parts of dendrobium, 12 parts of Chinese arborvitae kernel, 15 parts of root and vine of manyprickle acanthopanax, 12 parts of radix asparagi, 12 parts of danshen root, 12 parts of figwort root, 12 parts of gorgon euryale seeds, 4 parts of villous amomum fruit, 15 parts of coix seed, 19 parts of mulberry fruit, 11 parts of fruit of Chinese magnoliavine, 12 parts of lilium brownii, 7 parts of prepared milkwort root, 18 parts of barbary wolfberry fruit, 25 parts of donkey-hide gelatin, 25 parts of tortoise-plastron gelatin, and 25 parts of xylitol.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 9 folds of water for 12 h, with the water over the raw materials by 18 cm;

decoction: decocting the soaked drug materials over flame, firstly boiling the drug materials with high heat to sufficiently expand, then boiling the drug materials with low heat for 1.5 hours of decoction, then filtering the drug juice with gauze, then soaking filtered dregs of decoction with clear water and decocting the soaked dregs of decoction with low heat for 1 hour, repeated 3 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Embodiment 5:

A Chinese herbal oral paste for keeping balanced constitution includes the following raw material components in parts by weight: 12 parts of tangshen, 10 parts of largehead atractylodes rhizome, 15 parts of fuling, 6 parts of prepared liquorice root, 15 parts of glossy privet fruit, 10 parts of polygonatum odoratum, 10 parts of dwarf lilyturf tuber, 10 parts of flatstem milkvetch seed, 12 parts of Chinese yam, 12 parts of unprocessed hawthorn fruit, 15 parts of prepared fleeceflower root, 10 parts of milkvetch root, 10 parts of dried tangerine peel, 10 parts of angelica, 15 parts of dendrobium, 10 parts of Chinese arborvitae kernel, 12 parts of root and vine of manyprickle acanthopanax, 10 parts of radix asparagi, 10 parts of danshen root, 10 parts of figwort root, 10 parts of gorgon euryale seeds, 3 parts of villous amomum fruit, 12 parts of coix seed, 15 parts of mulberry fruit, 8 parts of fruit of Chinese magnoliavine, 10 parts of lilium brownii, 6 parts of prepared milkwort root, 15 parts of barbary wolfberry fruit, 20 parts of donkey-hide gelatin, 20 parts of tortoise-plastron gelatin, and 20 parts of xylitol.

The processing method thereof includes the following steps in sequence:

preparation of materials: measuring raw materials of formula amounts according to composition of the Chinese herbal oral paste, and cleaning raw materials, except tortoise-plastron gelatin, donkey-hide gelatin, and xylitol, for subsequent use;

soaking: soaking the cleaned raw materials with 9 folds of water for 9 h, with the water over the raw materials by 13 cm;

decoction: decocting the soaked drug materials over flame, firstly boiling the drug materials with high heat to sufficiently expand, then boiling the drug materials with low heat for 1.5 hours of decoction, then filtering the drug juice with gauze, then soaking filtered dregs of decoction with clear water and decocting the soaked dregs of decoction with low heat for 1 hour, repeated 3 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Experiment Example 1

Below a mouse anti-fatigue function experiment was conducted using the Chinese herbal oral paste prepared for keeping balanced constitution according to Embodiments 1-5, so as to explain the function that the Chinese herbal oral paste can maintain the balanced constitution under the influence of external factors (overstrain) and prevent transformation from the sub-healthy state to the biased constitution as well as keeping the healthy state.

Experimental Method 70 male SPF healthy mice were randomly divided into 7 groups, 10 in each group: (1) normal control group; (2) model group; (3) Embodiment 1; (4) Embodiment 2; (5) Embodiment 3; (6) Embodiment 4; (7) Embodiment 5; at 9:00 a.m. every day, the mice in groups (2)-(7) were placed into a plastic case with water depth of 0.8 cm and a size of 29 cm*18 cm*15 cm, taken out from the water case at 17:00 p.m. the same day, and fed normally. The models were prepared continuously for 21 d, at the same time, groups (3)-(7) were intragastrically administered with the Chinese herbal oral paste of respective embodiments the intragastric dosage is 20 g/kg of body weight, and the model group was intragastrically administered with equivalent weight of distilled water, while the normal control group was not given any stimulation or drug.

After the experiment was completed, indices of mice behavior observation were measured and biochemical criteria of the mice were detected for each group.

The indices measured are as follows:

(1) locomotor activity time: before the experiment was started, the mice were placed in independent chambers to get familiar to environment for 3 min. The number of times of activity of mice within 5 min was detected with a multifunctional mouse locomotor activity recorder under a peaceful condition, and the capability of mice locomotor activity was evaluated;

(2) step-through experiment: the step-through experiment was carried out with a step-through shuttle tester, with an electric shock voltage of 30 V, and an electric shock current limit of 0.50 mA. Before the experiment, the mice were placed into a bright chamber with their heads back to the opening, and got familiar to environment for 3 min. When the mice were exposed to the bright chamber, upon stimulation of light irradiation, their instinctive reaction was escaping to a dark chamber, and they would get shocked when entering the dark chamber, and returned back to the bright chamber, thus they would develop the memory that there was electricity in the dark box. The memory of the mice was evaluated by recoding the times of step-through shuttle of the mice within 5 min;

(3) desperation degree: an organic glass was perforated and hung to the mouse tail to make the mouse struggle, and the time that the mouse was motionless due to desperation within 5 min was added up to evaluate the mouse desperation degree;

(4) fatigue degree measurement: the exhaustive swimming time was measured to evaluate the mouse fatigue degree. An exhaustive swimming test was carried out by placing burden mice, whose tails were lied with a sinker with a weight of 7% of the mice, in a tap water pool with a water temperature of (25±1) ° C. and a water depth of 30-40 cm. The time from the mice falling into water to their nostrils sinking into water for 10 s and being unable to float to the water surface was recorded with a stopwatch, which was the exhaustive swimming time of the mice.

The experiment results show that compared with the normal control group, the mice of the model group have significantly decreased body weight, remarkably decreased locomotor activity times, significantly increased step-through shuttle times, obviously increased motionless time without 5 min, significantly decreased exhaustive time; compared with the model control group, the Chinese herbal oral paste of Embodiments 1-5 can improve the state and locomotor activity capability of the model mice, and keep the body weight, among which Embodiment 5 has the most remarkable effects.

It should be indicated that Embodiments 1-5 of the present invention are merely some of the embodiments for implementing the technical solutions of the present invention, and should not be construed as the scope of protection of the present invention merely limited to the above five embodiments, and a person skilled in the art can make further improvements on the basis of the present invention without departing from the principle and spirit of the present invention.

For example, the raw material components of the Chinese herbal oral paste of the present invention are not limited to those listed in respective embodiments, while other Chinese herbal medicines also can be added, to further perfecting the drug formulation of the Chinese herbal oral paste of the present invention.

For another example, in the process of the processing method for the Chinese herbal oral paste of the present invention, in the concentration step, when the drug juice is concentrated to the vegetarian paste, a wild jujube shell powder is added evenly with stirring. The wild jujube shell powder above is obtained by sufficiently smashing and grinding the wild jujube shell, with a particle size of 100-400 micrometers. The wild jujube shell powder has the main components of cellulose and lignin, has quite advanced pores in the powder particles, and is a natural drug carrier. When added to the Chinese herbal oral paste, the pores inside the wild jujube shell powder will be filled up with the drug components of the Chinese herbal oral paste. Since the cellulose and lignin cannot be digested or absorbed in vivo, they can serve an effect of sustained release, and a small part of the drug components stored in the wild jujube shell powder can be released continuously, so that the drug is present in the digestive system for an extended period of time. The phenomenon that the drug components are wasted as the digestive system cannot absorb a large amount of drug components within a short period of time will not occur. The wild jujube shell powder is added in an amount of 1%-3% of the gelatin type drugs, and should not be used in an excessive amount, because the excessive amount, on one hand, will deteriorate the form quality of the oral paste, and on the other hand, will increase the burdens of the intestines and stomach as it cannot be absorbed by the human body.

The descriptions above are only preferred embodiments of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

What is claimed is:

1. A Chinese herbal oral paste for keeping balanced constitution, comprising the following raw material components in parts by weight: 6-18 parts of *Codonopsis pilosula,* 5-15 parts of largehead atractylodes rhizome, 8-22 parts of fuling, 2-10 parts of prepared liquorice root, 7-23 parts of glossy privet fruit, 5-15 parts of *polygonatum odoratum,* 5-15 parts of dwarf lilyturf tuber, 5-15 parts of flatstem milkvetch seed, 6-18 parts of Chinese yam, 6-18 parts of unprocessed hawthorn fruit, 7-23 parts of prepared fleeceflower root, 5-15 parts of milkvetch root, 5-15 parts of dried tangerine peel, 5-15 parts of angelica, 8-22 parts of *dendrobium,* 6-14 parts of Chinese arborvitae kernel, 7-17 parts of root and vine of manyprickle acanthopanax, 5-16 parts of radix asparagi, 5-15 parts of danshen root, 6-14 parts of figwort root, 5-14 parts of gorgon euryale seeds, 1-5 parts of villous amomum fruit, 6-18 parts of coix seed, 7-23 parts of mulberry fruit, 3-14 parts of fruit of Chinese magnoliavine, 4-16 parts of lilium brownii, 3-9 parts of prepared milkwort root, 7-23 parts of barbary wolfberry fruit, 10-30 parts of donkey-hide gelatin, 10-30 parts of tortoise-plastron gelatin, and 10-30 parts of xylitol.

2. The Chinese herbal oral paste for keeping balanced constitution of claim 1, comprising the following raw material components in parts by weight: the *Codonopsis pilosula* is 9-15 parts by weight, the largehead atractylodes rhizome is 8-12 parts by weight, the fuling is 11-19 parts by weight, the prepared liquorice root is 4-8 parts by weight, the glossy privet fruit is 11-19 parts by weight, the *polygonatum odoratum* is 8-12 parts by weight, the dwarf lilyturf tuber is 8-12 parts by weight, the flatstem milkvetch seed is 8-12 parts by weight, the Chinese yam is 9-15 parts by weight, the unprocessed hawthorn fruit is 9-15 parts by weight, the prepared fleeceflower root is 11-19 parts by weight, the milkvetch root is 8-12 parts by weight, the dried tangerine peel is 8-12 parts by weight, the angelica is 8-12 parts by weight, the *dendrobium* is 12-18 parts by weight, the Chinese arborvitae kernel is 8-12 parts by weight, the root and vine of manyprickle acanthopanax are 9-15 parts by weight, the radix asparagi is 8-12 parts by weight, the danshen root is 8-12 parts by weight, the figwort root is 8-12 parts by weight, the gorgon euryale seeds are 8-12 parts by weight, the villous amomum fruit is 2-4 parts by weight, the coix seed is 9-15 parts by weight, the mulberry fruit is 11-19 parts by weight, the fruit of Chinese magnoliavine is 5-11 parts by weight, the lilium brownii is 8-12 parts by weight, the prepared milkwort root is 5-7 parts by weight, the barbary wolfberry fruit is 12-18 parts by weight, the donkey-hide gelatin is 15-25 parts by weight, tortoise-plastron gelatin is 15-25 parts by weight, and the xylitol is 15-25 parts by weight.

3. The Chinese herbal oral paste for keeping balanced constitution of claim 1, comprising the following raw material components in parts by weight: the *Codonopsis pilosula* is 12 parts by weight, the largehead atractylodes rhizome is 10 parts by weight, the fuling is 15 parts by weight, the prepared liquorice root is 6 parts by weight, the glossy privet fruit is 15 parts by weight, the *polygonatum odoratum* is 10 parts by weight, the dwarf lilyturf tuber is 10 parts by weight, the flatstem milkvetch seed is 10 parts by weight, the Chinese yam is 12 parts by weight, the unprocessed hawthorn fruit is 12 parts by weight, the prepared fleeceflower root is 15 parts by weight, the milkvetch root is 10 parts by weight, the dried tangerine peel is 10 parts by weight, the angelica is 10 parts by weight, the *dendrobium* is 15 parts by weight, the Chinese arborvitae kernel is 10 parts by weight, the root and vine of manyprickle acanthopanax are 12 parts by weight, the radix asparagi is 10 parts by weight, the danshen root is 10 parts by weight, the figwort root is 10 parts by weight, the gorgon euryale seeds are 10 parts by weight, the villous amomum fruit is 3 parts by weight, the coix seed is 12 parts by weight, the mulberry fruit is 15 parts by weight, the fruit of Chinese magnoliavine is 8 parts by weight, the lilium brownii is 10 parts by weight, the prepared milkwort root is 6 parts by weight, the barbary wolfberry fruit is 15 parts by weight, the donkey-hide gelatin is 20 parts by weight, tortoise-plastron gelatin is 20 parts by weight, and the xylitol is 20 parts by weight.

4. A processing method for the Chinese herbal oral paste for keeping balanced constitution of claim 1, comprising the following steps in sequence: preparation of materials, soaking, decoction, concentration, and collecting an oral paste.

5. The processing method for the Chinese herbal oral paste for keeping balanced constitution of claim 4, wherein the step of preparation of materials is: measuring raw materials of formula amounts according to composition of the Chinese herbal oral paste, and cleaning raw materials, except tortoise-plastron gelatin, donkey-hide gelatin, and xylitol, for subsequent use.

6. The processing method for the Chinese herbal oral paste for keeping balanced constitution of claim 5, wherein the soaking step is: soaking the cleaned raw materials with 8-10 folds of water for 8-15 h, with the water over the raw materials by 10-20 cm.

7. The processing method for the Chinese herbal oral paste for keeping balanced constitution of claim 6, wherein the decoction step is: decocting the soaked drug materials over flame, firstly boiling the drug materials with high heat to sufficiently expand, then boiling the drug materials with low heat for 1-2 hours of decoction, then filtering the drug juice with gauze, then soaking filtered dregs of decoction with clear water and decocting the soaked dregs of decoction with low heat for 1 hour, repeated 2-4 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

8. The processing method for the Chinese herbal oral paste for keeping balanced constitution of claim 7, wherein the concentration step is: boiling and skimming the supernatant liquid resulted in the decoction step, followed by decoction concentration and stirring with gentle heat, until a drug liquid does not disperse when being dropped on paper, to obtain a vegetarian paste.

9. The processing method for the Chinese herbal oral paste for keeping balanced constitution of claim 8, wherein the step of collecting an oral paste is: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

10. The processing method for the Chinese herbal oral paste for keeping balanced constitution of claim 9, wherein the melting step is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

11. A processing method for the Chinese herbal oral paste for keeping balanced constitution of claim 2, comprising the following steps in sequence: preparation of materials, soaking, decoction, concentration, and collecting an oral paste.

12. The processing method for the Chinese herbal oral paste for keeping balanced constitution of claim 11, wherein the step of preparation of materials is: measuring raw materials of formula amounts according to composition of the Chinese herbal oral paste, and cleaning raw materials, except tortoise-plastron gelatin, donkey-hide gelatin, and xylitol, for subsequent use.

13. The processing method for the Chinese herbal oral paste for keeping balanced constitution of claim 12, wherein the soaking step is: soaking the cleaned raw materials with 8-10 folds of water for 8-15 h, with the water over the raw materials by 10-20 cm.

14. The processing method for the Chinese herbal oral paste for keeping balanced constitution of claim 13, wherein the decoction step is: decocting the soaked drug materials over flame, firstly boiling the drug materials with high heat to sufficiently expand, then boiling the drug materials with low heat for 1-2 hours of decoction, then filtering the drug juice with gauze, then soaking filtered dregs of decoction with clear water and decocting the soaked dregs of decoction with low heat for 1 hour, repeated 2-4 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

15. The processing method for the Chinese herbal oral paste for keeping balanced constitution of claim 14, wherein the concentration step is: boiling and skimming the supernatant liquid resulted in the decoction step, followed by decoction concentration and stirring with gentle heat, until a drug liquid does not disperse when being dropped on paper, to obtain a vegetarian paste.

16. The processing method for the Chinese herbal oral paste for keeping balanced constitution of claim 15, wherein the step of collecting an oral paste is: pouring xylitol, and melted tortoise-plastron gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

17. The processing method for the Chinese herbal oral paste for keeping balanced constitution of claim 16, wherein the melting step is: smashing lumps of tortoise-plastron gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

18. A processing method for the Chinese herbal oral paste for keeping balanced constitution of claim 3, comprising the following steps in sequence: preparation of materials, soaking, decoction, concentration, and collecting an oral paste.

19. The processing method for the Chinese herbal oral paste for keeping balanced constitution of claim 18, wherein the step of preparation of materials is: measuring raw materials of formula amounts according to composition of the Chinese herbal oral paste, and cleaning raw materials, except tortoise-plastron gelatin, donkey-hide gelatin, and xylitol, for subsequent use.

20. The processing method for the Chinese herbal oral paste for keeping balanced constitution of claim 19, wherein the soaking step is: soaking the cleaned raw materials with 8-10 folds of water for 8-15 h, with the water over the raw materials by 10-20 cm.

* * * * *